United States Patent [19]

Newton et al.

[11] Patent Number: 4,865,811
[45] Date of Patent: Sep. 12, 1989

[54] APPARATUS FOR AUTOMATIC CHEMICAL ANALYSIS

[75] Inventors: Raymond Newton, Ware; David Malcolm-Lawes, Buckhurst Hill, both of England

[73] Assignee: Biotec Instruments Limited, Luton, England

[21] Appl. No.: 159,366
[22] PCT Filed: Jun. 26, 1987
[86] PCT No.: PCT/GB87/00448
§ 371 Date: Feb. 22, 1988
§ 102(e) Date: Feb. 22, 1988
[87] PCT Pub. No.: WO88/00347
PCT Pub. Date: Jan. 14, 1988

[30] Foreign Application Priority Data

Jul. 1, 1986 [GB] United Kingdom ............. 8615979
Jan. 5, 1987 [GB] United Kingdom ............. 8700075

[51] Int. Cl.⁴ .................................................. G01N 35/08
[52] U.S. Cl. .................................................. 422/81; 422/82; 436/52; 436/53; 73/863.71
[58] Field of Search ............... 73/863.71; 422/81, 82; 436/52, 53

[56] References Cited
U.S. PATENT DOCUMENTS 4,177,677 12/1979 Ruzicka et al. ............. 73/863.71
4,207,074 6/1980 Suzuki ............................. 422/81
4,224,033 9/1980 Hansen et al. ................... 422/81
4,272,483 6/1981 Schick ............................. 422/67
4,283,262 8/1981 Cormier et al. ............ 204/195 M
4,362,699 12/1982 Verlander et al. ............. 422/131
4,411,157 10/1983 Babin et al. ................. 73/864.81
4,713,974 12/1987 Stone ........................... 73/864.23

FOREIGN PATENT DOCUMENTS 10175 1/1985 Japan .

Primary Examiner—Michael S. Marcus
Assistant Examiner—D. John Griffith, Jr.
Attorney, Agent, or Firm—Lee & Smith

[57] ABSTRACT

A sample duct in a carrier line is isolated by three-way valves blocking the flow of carrier or flushing liquid from reservoirs. The sample duct may be connected to a loading syringe and to a sample reservoir respectively by the valves. When the sample duct is connected into the carrier line, pressurized carrier fluid may convey the sample for analysis through a manifold comprising valves through which reagents may be introduced from reservoirs. The sample then passes through a thermostatically controlled reaction tube to a valve which switches it between waste and an outlet leading to a detector for analysis. The carrier and flushing fluids and the reagents are pressurized by gas from an inlet which is conveyed via an overpressure vent to the reservoir by lines. Rigid inert tubing is used throughout the carrier line, sample duct, manifold and reaction tube.

10 Claims, 10 Drawing Sheets

| OPERATION | VALVE PATTERN | | | | | | | |
|---|---|---|---|---|---|---|---|---|
| | 86 | 74 | 76 | 78 | 80 | 82 | 84 | 88 |
| DEFAULT / FLUSH | NO | NO | NO | NO | NO | NO | NO | NO |
| REAGENT LOAD | NO | (USER SELECTED) | NO | NO | NO | NO | NO | |
| AWAITING SAMPLE | NC | NO | NO | NO | NO | NC | NO | NO |
| ANALYSE | NC | NO | NO | NO | NO | NC | NC | NC |
| STOP FLOW | NC | NO | NO | NO | NO | NO | NO | NO |

Fig. 11

APPARATUS FOR AUTOMATIC CHEMICAL ANALYSIS

FIELD OF THE INVENTION

This invention relates generally to apparatus for automatic chemical analysis, and more particularly apparatus for and a method of flow injection analysis.

BACKGROUND TO THE INVENTION

Flow injection analysis (FIA) is employed in wet chemistry for the analysis of chemical samples. A defined volume of the sample is conveyed by a liquid carrier stream to a flow-through detector in which the sample is analysed. Provision is made for the addition of a reagent to the sample being conveyed, whereafter the conveyed sample and reagent pass through a reaction tube before entry into the detector.

PRIOR ART

Apparatus for fluid injection analysis is known from UK patent specification No. 2104657, wherein a relatively complex valve is provided which in a first position acts to divert the flow of carrier fluid through the valve independently of the sample duct, thereby to enable the sample duct to be loaded, and in a second position passes the carrier flow through the sample duct, the valve acting while passing between the first and second positions to cut off the flows of carrier, sample and reagent. In this known analysis system, the carrier liquid is conveyed by positive pressure displacement instead of by the use of a peristaltic pump, as is the conventional practice.

OBJECT OF THE INVENTION

It is an object of this invention to provide improved apparatus for and an improved method of flow injection analysis which are flexible in operation and offer high versatility in usage.

THE INVENTION

According to one aspect of the invention, there is provided apparatus for flow injection analysis, in which a sample to be analysed is loaded into a sample duct of predetermined volume from which it is conveyed by pressurised carrier fluid with an added reagent to a reaction tube, wherein the sample duct is positioned in a carrier line between isolating valves operable to stop the flow of carrier fluid and to isolate the sample duct from the carrier line in order to provide a connection to a sample loading means.

According to another aspect of the invention, there is provided a method of flow injection analysis wherein a sample to be analysed and contained in a sample duct is conveyed to a reaction tube by pressurised carrier fluid, with a pressurised reagent being added upstream or downstream of the sample, and wherein the sample duct is located in a carrier line between a pair of isolating valves, the method including the steps of operating a valve on one side of the sample duct to connect a sample inlet to the sample duct and isolate the sample duct from the carrier line, operating the other valve to connect the sample duct to a suction inlet and isolate the sample duct from the carrier line, loading the sample into the sample duct, and operating the two valves to connect the sample duct in to the carrier line.

In a preferred arrangement, two three-way isolating valves are provided, one on the upstream and one on the downstream side of the sample duct.

Between the isolating valves and between the sample duct and the valve providing for connection to the suction inlet, an additional three-way valve is preferably provided, enabling sample surplus to the said predetermined volume to be passed to waste.

On the upstream side of the upstream isolating valve, one or more further three-way valves may provide for the carrier line to be connected to any one of a plurality of carrier and/or flushing liquids.

On the downstream side of the downstream isolating valve, but upstream of the reagent manifold, a still further three-way valve may provide for priming, allowing for intake of a small amount of sample and its ejection to waste before loading the sample duct with the predetermined volume to be analysed.

The sample loading means may conveniently comprise a solenoid operable syringe which acts via the upstream isolating valve to suck the sample into the sample duct via the downstream isolating valve.

The reagent manifold may comprise a series of three-way valves, each providing for connection with an individual reagent reservoir. Any one or more of the said series of valves may be provided for addition of any one or more reagents to the sample to be analysed.

Downstream of the reagent manifold, the reaction tube is preferably thermostatically controlled, and may be followed by yet another three-way valve which provides connections either to waste or to an outlet leading to the detector.

Both the carrier and/or flushing liquids and the reagents are driven by positive pressure displacement, pressurisation preferably being effected from a common gas inlet and protected by an overpressure vent. Conveyance by positive pressure displacement enables rigid tubing or ducting to be employed throughout the apparatus, thus affording greater precision than the flexible tubing normally used with systems driven by peristaltic pumps.

The sample is drawn from a sample reservoir which may readily be incorporated in an automatic sample changer, and programmed control is possible for example to enable on-stream monitoring or a succession of analyses for different sequential samples each for one or more analytes.

The various three-way valves employed in the apparatus may be operated manually, or automatically in a programmed sequence in the case of computerised control.

BRIEF DESCRIPTION OF THE DRAWINGS

The apparatus and method in accordance with the invention will now be exemplified with reference to the accompanying drawings in which:

FIG. 11. is a table of the operating sequence of the valves of FIG. 6; and

DESCRIPTION OF EMBODIMENTS

Figure 1:
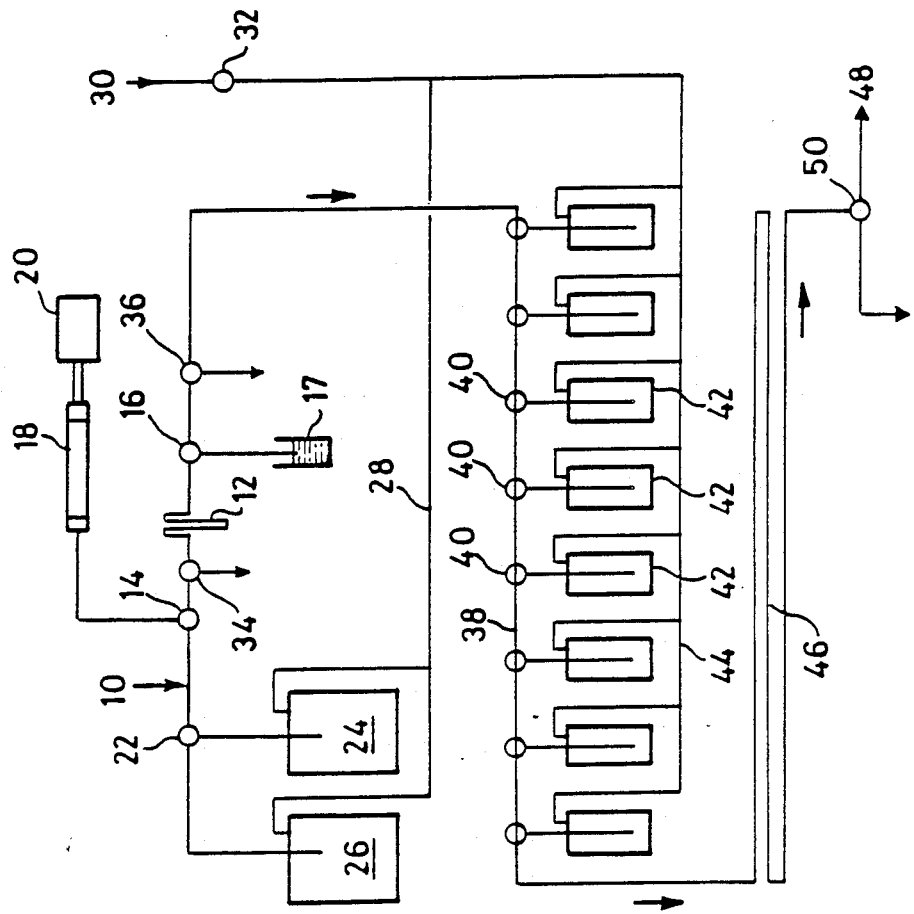
FIG. 1 shows one embodiment of apparatus according to the invention in diagrammatic form.

Referring first to FIG. 1 of the drawings, the reference 10 generally denotes a carrier line. The line 10 includes a sample duct or loop 12 which is located between upstream three-way isolating valve 14 and downstream three-way isolating valve 16. The valves 14 and 16 enable the sample duct 12 either to be connected on-stream in the carrier line 10 or to be isolated from the carrier line and be connected on the downstream side to a sample reservoir 17 and on the upstream side to a sample loading means comprising a load syringe 18 operable by a solenoid 20.

A three-way valve 22 upstream of the upstream isolating valve 14 enables either a carrier liquid from a reservoir 24 or a flushing liquid from a reservoir 26 to be taken into the carrier line. More than two such carrier/flushing agent reservoirs may be provided, together with the appropriate number of three-way valves.

Supply of carrier liquid (or flushing agent) into the carrier line 10 is by positive pressure displacement, enabled by a gas line 28 supplied with gas such as nitrogen gas under pressure from a gas inlet 30 via an overpressure vent 32. A suitable gas supply pressure is of the order of 5 to 15 psig (0.35 to 1.05 kg/cm$^2$), giving a flow rate through a downstream detector (not shown but conveniently a computer controlled spectrophotometer) of 0.1 to 5 ml per minute, with 1 ml per minute possibly being a preferred value.

A three-way valve 34 connectable to waste is provided between the upstream isolating valve 14 and the sample loop 12, and another three-way valve 36 connectable to waste is connected in the carrier line just downstream of the downstream isolating valve 16.

Downstream of the sample loading system, the carrier line 10 leads to a reagent manifold 38, where a series of three-way valves 40 enable any one or more of a number of reagents contained in reservoirs 42 to be added to a sample being conveyed along the carrier line. Supply of reagent is also by positive pressure displacement, enabled by the gas line 44 fed from the same gas inlet 30.

The sample/reagent mixture passes to a thermostatically controlled reaction tube 46 and thence to an outlet 48 leading to the detector via a three-way valve 50 having an alternative outlet to waste. The reaction tube will typically be controlled to operate in the range from room temperature up to 100 degrees Celsius.

All ducting 12 and manifold 38 is in the form of rigid inert tubing.

In use, a sample (typically in an amount from 20 to 200 microliters) is drawn into the sample duct 12 by operating the load syringe 18 while the isolating valves 14 and 16 are operated to isolate the region of the carrier line 10 between them which contains the sample duct. Surplus sample passes to waste by operating valve 34, releasing the load syringe 18 and then operating the upstream isolating valve 14 to flush the space between said valve 14 and said waste valve 34.

After sample loading, the isolating valves 14 and 16 are operated to reconnect the sample duct 12 into the carrier line 10, whereby operation of the valve 22 causes carrier liquid to enter the carrier line to convey the sample downstream. As the reagent passes any one or more of the valves 40 in the reagent manifold 38, the appropriate valve 40 is operated to cause a selected reagent or reagents to be added. For this purpose the appropriate valve 40 is operated several times to inject a required amount of reagent, typically ten times for a period of 1 second each time in order to supply 200 microliters of reagent for mixing with a 200 microliter sample. Flow then continues to take the sample/reagent mixture to the reaction tube 46.

The sample loading system permits priming between samples by intake of a small amount of sample, followed by its ejection through the downstream waste valve 36. Full flushing of the system is enabled by opening the valve 22 to the flushing agent reservoir 24 and the valve 50 to waste. It is to be noted, however, that priming and/or flushing is not an essential intermediate step between successive samplings, which is advantageous if several sample aliquots are to be successively drawn from the same reservoir, for example to test for different analytes.

It is to be noted that incorporation of an automatic sample changer is readily possible, and also that there is no limit to the number of reagent reservoirs which may connect with the reagent manifold.

The system may be computer controlled with any chosen program which produces repeated valve operations, sample loadings, and reagent loadings in any chosen sequence, for example for on-stream monitoring or a complex series of analysis involving differing samples, differing analytes and differing reagents.

The system is particularly suited to use in the field, since a 12 volt d.c. supply is sufficient for the operation of electrical components and a nitrogen cylinder is sufficient to enable flow by positive gas displacement. This last mentioned means of fluid conveyance is also advantageous to the use of a detector in the form of a visible/UV spectrophotometer, since the pulsating flow associated with the use of peristaltic pumps is avoided.

Another important advantage of the system is that it enables the flows of carrier, sample and reagent to be carried out by means of rigid inert tubing and inert valves, enabling use with both organic materials and strong inorganic acids and bases, which is generally not possible with systems driven by peristaltic pumps.

Various modifications of the illustrated and described arrangement are possible within the scope of the invention hereinbefore defined, and in particular reference is made to FIGS. 2 to 10 of the drawings and the following description relating thereto.

In essence, FIA relies on the introduction of a sample into a continuously flowing stream of carrier liquid with which the sample reacts while travelling to a detector. The detector monitors some property of the liquid which undergoes a change according to the extent of the selective reaction which has occurred between the injection of the sample and its arrival at the detector. The principal advantage of this technique over the older, air-segmented continuous-flow analyser approach is that the incompressibility of the carrier liquid at the pressures used in FIA (typically a few psi) allows the time interval between injection and detection to be reproduced with high accuracy. This in turn allows reaction products to be monitored without waiting for a steady-state to be reached, so permitting a high rate of sampling to be achieved.

Figure 2:
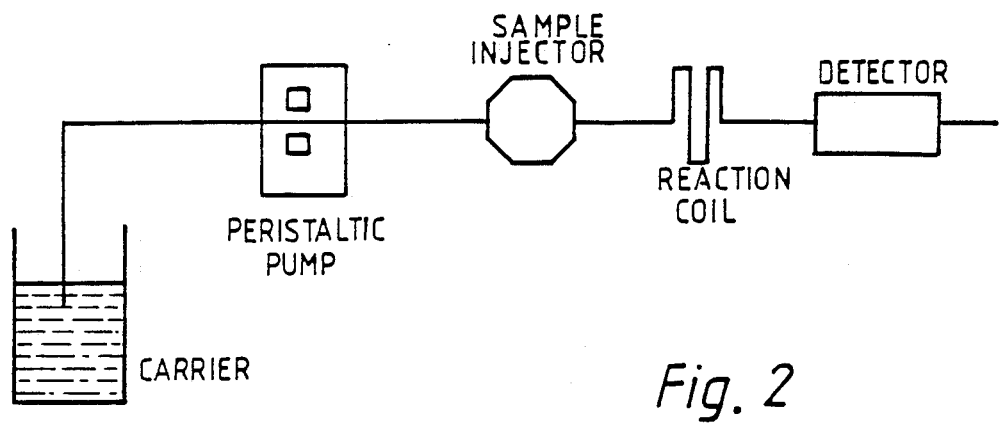
FIG. 2 is a schematic representation of a known manifold used for FIA.

A simple FIA manifold is illustrated in FIG. 2. A sample aliquot is injected into a carrier stream containing reagents (normal FIA), or by injection of reagents into a flow containing the sample (inverse FIA). Both approaches result in limited flexibility because relatively large volumes of either sample or reagent are required, and because complex reagents or reagents with a short shelf-life cannot be provided easily from a single reservoir over a long period.

The normal method of propelling the carrier stream in FIA is to utilise a peristaltic pump in order to prevent reagents coming into contact with material other than the tubing. Peristaltic pumps have two deficiencies. Firstly they are notoriously unreliable because the tubing ages, and secondly they generate pressure waves during operation which can give rise to refractive index and concentration variations with the detector's flow cell, i.e. noise superimposed on the desired signal.

The present invention provides a novel apparatus or instrument for performing selective reaction analysis. The objective in the design of the instrument was to retain the advantages of FIA (highly reproducible timing, so that reactions need not go to completion before the detection process) while discarding those aspects of the technique which seem undesirable (peristalsis and limited flexibility). An experimental version of the instrument, using a standard analysis for phosphate, is described below.

Figure 3:
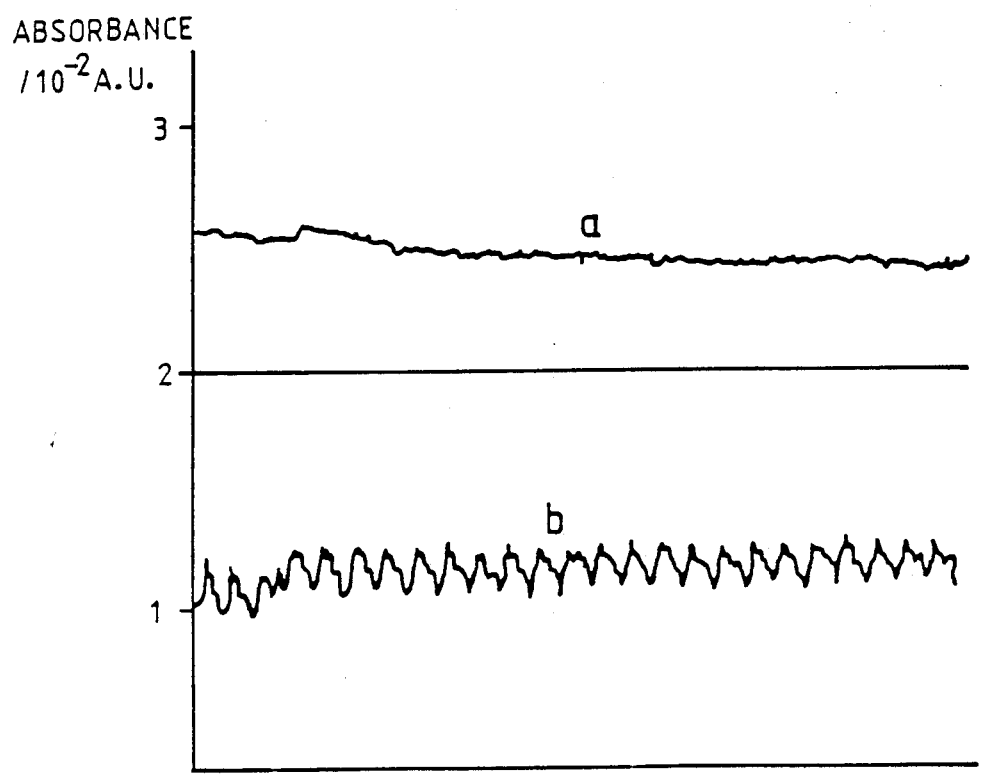
FIG. 3 shows baseline noise level recorded using (a) gas pressure and (b) peristaltic pump drive carrier flow.

Essentially the instrument uses a carrier flow of a low cost liquid which is inert (in the sense that it does not contribute to the reaction), and into which both sample and reagents are injected through computer controlled valves. The design of the analyser abandons the use of peristaltic pumps in favour of gas pressure propulsion of the carrier flow. This has the advantage of producing a liquid flow which gives rise to less noise in the detector signal than can be obtained from peristaltic pumps. A typical example of the reduced noise as absorbance is shown in FIG. 3, where the signal monitored used a spectrophotomeric detector (type Cecil CE 5095) operating at 500 nm with a flow of water pumped through the flow cell. The signal trace is shown at (a) for pressure propulsion, and at (b) for peristaltic pumping. In each case the flow rate was approximately 1 ml/min, and the full scale range of the detector was 0.05 Angstrom Units (hereafter AU).

Figure 4:
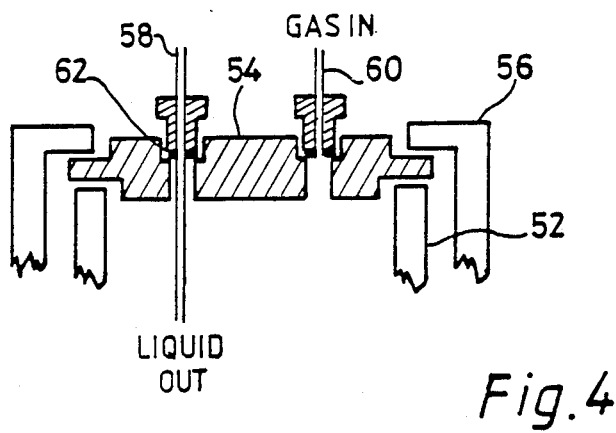
FIG. 4 is a section through the cap of a pressurised reservoir which may be used in the apparatus.

Referring to FIG. 4, the carrier and flushing liquids and the reagents are stored separately in Schott Duran bottles 52 (generally 1000 and 500 ml capacities respectively) fitted with closures 54 fabricated from ptfe (poly-tetra-fluoro-ethylene) and held in place by a normal bottle cap 56 through which a 30 mm hole had been bored. Two ptfe tubes 58, 60 are connected to each reservoir using Cheminert couplings as illustrated in FIG. 4. One tube 60 carries the pressurising gas and terminates at a hole in the closure. The other carries the liquid from the reservoir and passes through the closure, the tube-closure seal being completed by a small silicone O-ring 62.

Carrier, flushing liquid, reagent and sample flows are controlled using solenoid valves connected together as a manifold using 1/16th inch ptfe tubing. Solenoid valves are employed for automated reagent mixing and carrier control. For this experimental model of the automatic analyser Lee valves (type LFYX0500200AB) are used, operated by 12 V logic levels. The structure of one such valve is shown schematically in FIG. 5 and operation consists essentially of closing one of the two pathways 64, 66 between a common connection 68 and a normally open channel 70 and a normally closed channel 72. The channel 70 is open unless current passes through the solenoid, in which case the actuator moves to the right, closing the channel 70 and leaving channel 72 open.

Figure 5:
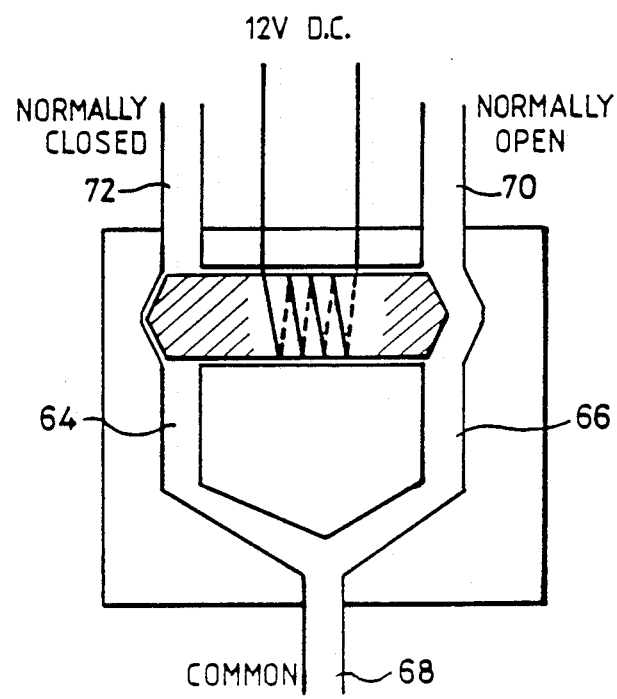
FIG. 5 shows the structure of a solenoid valve of the apparatus.

As an alternative to the valve of FIG. 5, the following valves may be used: type 161T011 (2 way valve) and type 161T031 (3 way valve) made by Neptune Research Limited of 6 Lombardi Place, Maplewood, N.J., USA.

Figure 6:
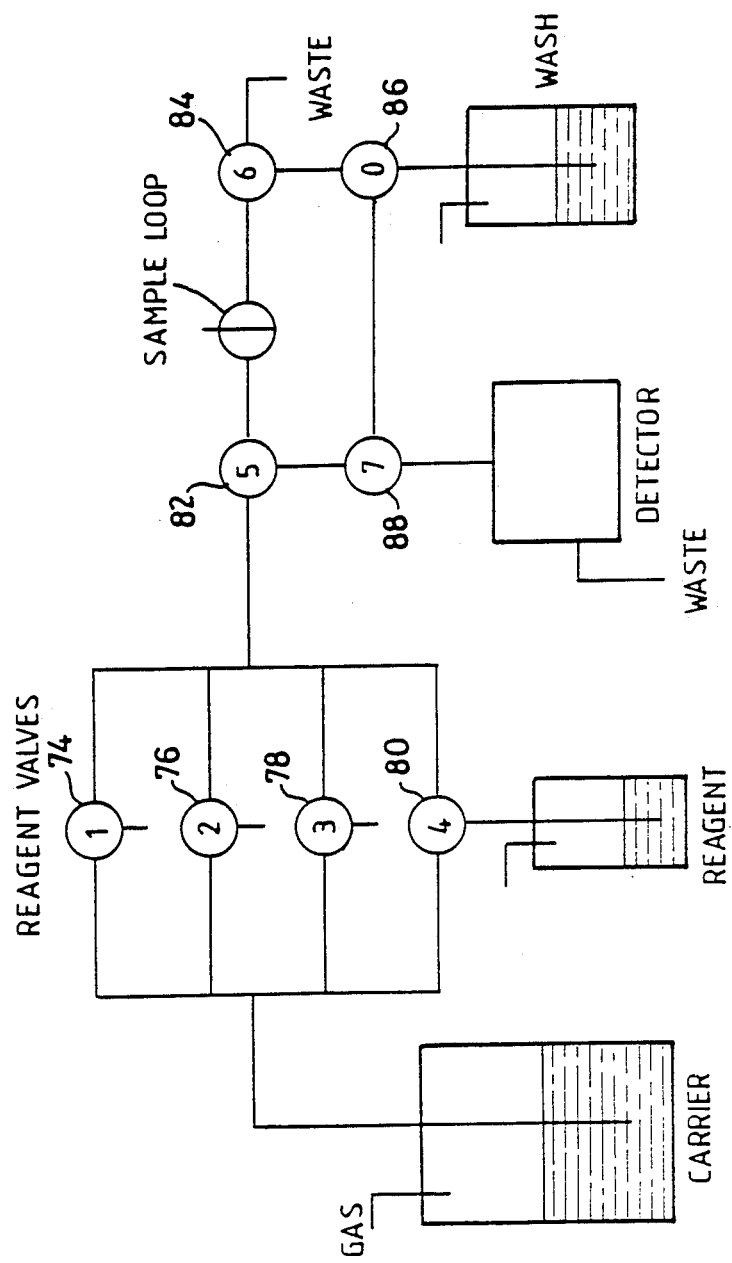
FIG. 6 is a schematic diagram showing modified valve interconnections.

The valve connection manifold is shown in FIG. 6. For this experimental instrument a limit of four reagent reservoirs was set by the number of valves available, although there is no reason why a much larger number could not be employed. Valves 74–80 allow selected reagent to enter the flow by replacing reagent, and the four valves are equidistant from a mixing point (valve 82) to simplify injection timing. The sample loop may be filled by needle injection, suction or indeed any automated technique.

Reagent or a mixture of reagents is allowed to fill the section between valves 82 and 84, then valve 82 is closed (along with any reagent valves previously opened) and the sample loop is switched in. At this point the pathway between valves 82 and 84 contains a reagent-sample-reagent sandwich of precisely reproducible volumes, and closure of valves 86, 84, 82, and 88 causes this sandwich to be passed through valve 88 to the detector. Once the reaction product has been measured, valves 82 and 84 may be opened and the pathway in between flushed by wash liquid (which may be of the same composition as the carrier), which also flushes the reagent valves and interconnecting tubes.

The sequence of valve operations is summarised in FIG. 11, in which NO refers to the normally open state of a valve and is the condition when it is logicaly off, and NC refers to the normally closed state. The "awaiting sample" condition (which halts flow through valve 82 and the detector) is required only for manual sample loading, where there may be a significant delay between reagent assembly and the operator actually loading the sample. For manual sample injection, the operation of introducing the sample into the reagent sandwich is sensed by an optical sensor (not shown) attached to the injection valve. This allows a computer to start the timing sequence for the remainder of the analysis— which may require immediate switching to the "analyse" state.

The important volume, and hence length of interconnecting tubing, is that of the segment between valves 82 and 84—and, of course, the sample loop volume itself. There are two parts to this segment, one either side of the sample loop, and these must be large enough to ensure that there is always an excess of reagent over sample as the two travel to the detector. On the other hand, making these volumes small allows for considerable economy in the use of reagents. For the purposes of this instrument it was assumed that the user would want a compromise between the sensitivity (related to peak height) and sample throughput rate (inversely proportional to peak width), and the height-to-width ratio of detected peaks was taken as suitable criterion for parameter optimisation. It was found that, using a flow rate of 1.5 ml/min, a maximum value of the height-to-width ratio was obtained for a sample loop volume of 175 microliters, with volumes of 40 and 140 microliters for the volumes of tubing on the valve 82 and valve 84 side of the loop respectively.

For the prototype analyser a spectrophotometric detector was chosen, as this allowed many classical reactions to be used relatively easily—much as in conventional flow injection analysis. Two detectors have been used to date, one a filter colorimetric detector, and the other a Cecil uv-vis spectrometer fitted with a 100 microliter flow cell.

Figure 7:
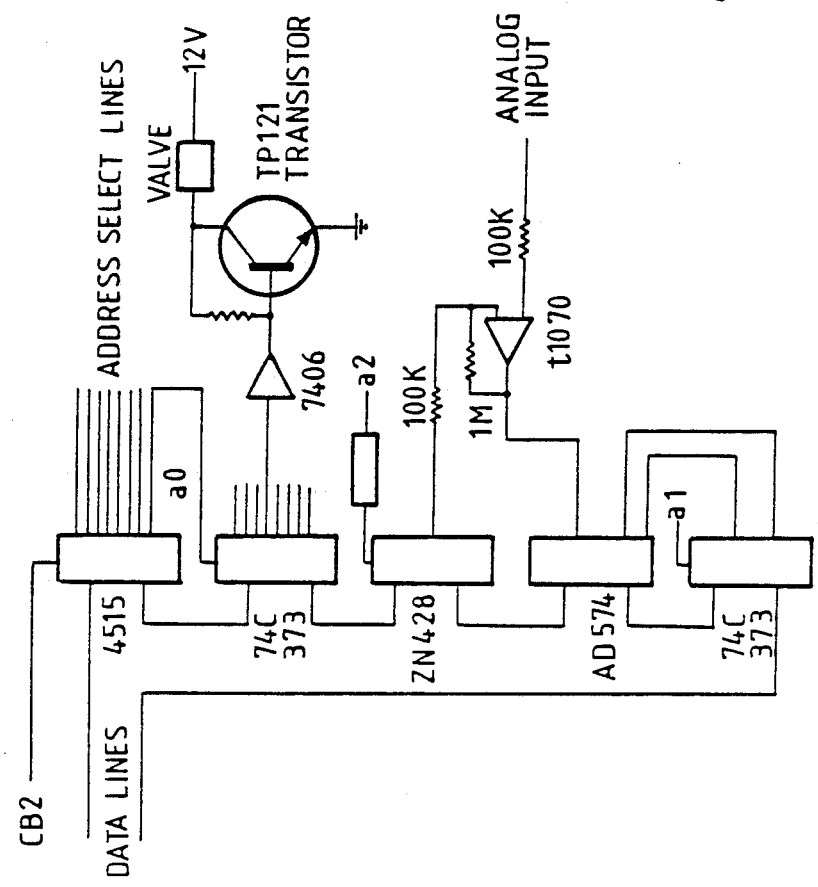
FIG. 7 shows principal elements of a computer interface for use with the apparatus.

The instrument is connected to a Commodore 64 microcomputer using a multifunction interface unit, as shown in outline in FIG. 7. The output from the detector is monitored using a dynamic analog interface which allows a reading over the range 0–1 V with a precision of approximately 10 microvolts. Each valve is controlled by a logic output via an interface based on a TP121 transistor in series with the valve solenoid. The sample-loaded sensor is connected to the computer's paddle port, where the change in resistance of a photodiode forming part of a standard slotted opto-switch (RS Components) as the loop valve turned is monitored.

Figure 8:
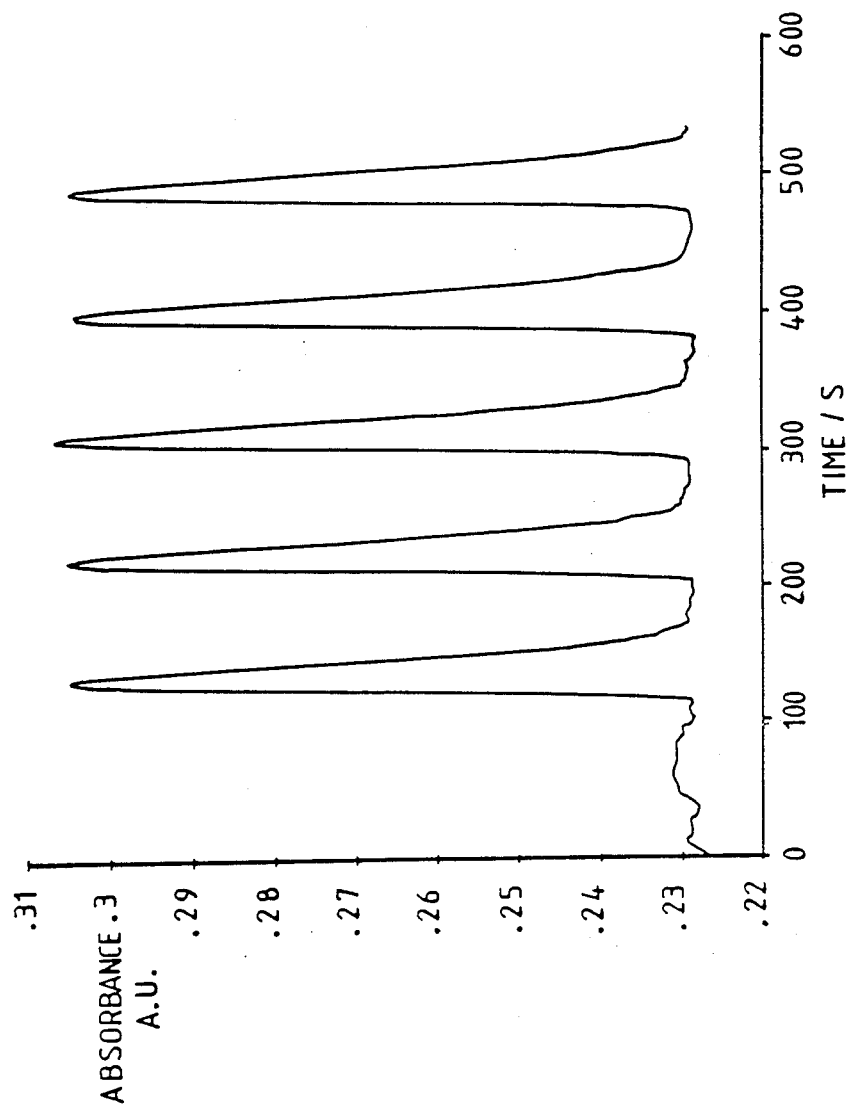
FIG. 8 is a trace showing absorbance peaks recorded of a sample containing phosphate.

FIG. 8 is an absorbance/time trace showing the uncorrected output recorded from five successive samples of phosphate (approximately 500 uM) monitored using the colour developed by the reaction with a mixture of sodium molybdate ($3.2 \times 10^{-2}$M) and ascorbic acid ($2.7 \times 10^{-3}$M). The product was monitored at 500 nm.

Clearly the instrument gives reproducible results and the sensitivity is of the same order as one would expect from conventional flow injection analysis. However, the technique used does give rise to two features which become superimposed on the detector baseline. The first arises from the refractive index change brought about by the introduction of reagent into the carrier flow. This results in a lens-like liquid/liquid interface which focusses the light passing through the flow cell more effectively than a homogeneous liquid. The net result is an increase in transmission and a negative-going peak (or trough) on the absorbance record as the reagent-sample-reagent sandwich passes through the cell. Because most reagents will have a different absorbance from the carrier liquid at the monitoring wavelength, the passage of reagent through the cell generally produces a second feature—a positive going absorbance signal immediately following the trough.

Figure 9:
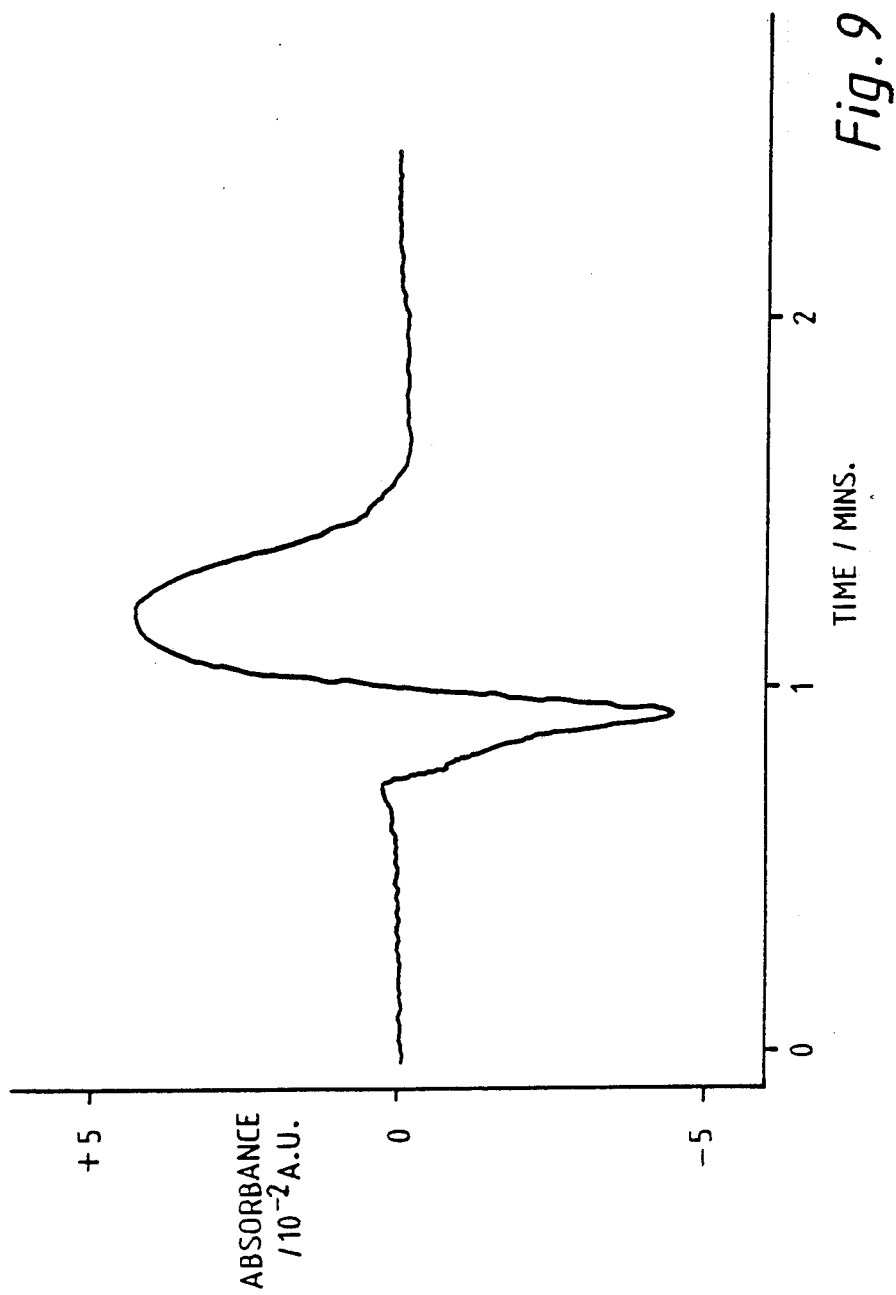
FIG. 9 shows a trace of baseline fluctuation cause by the introduction of a strong reagent into a distilled water carrier.
Figure 10:
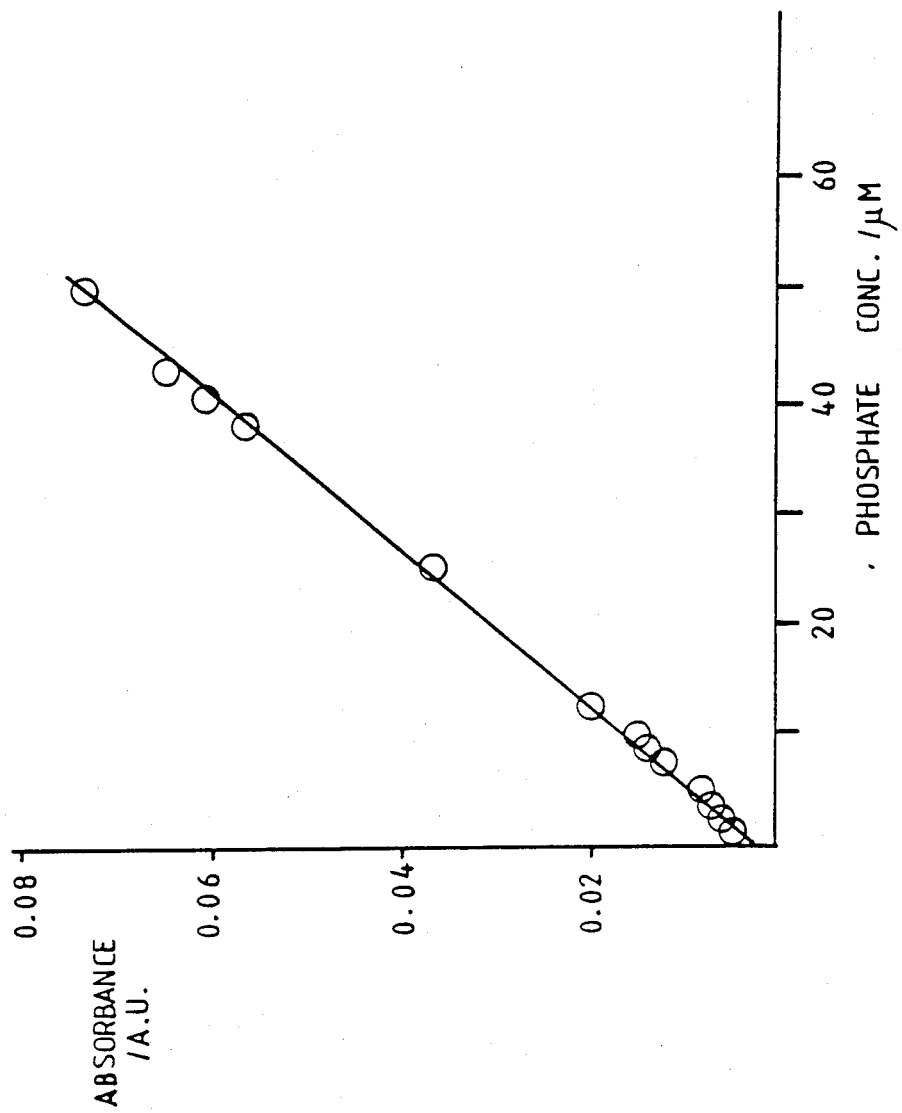
FIG. 10 is a graph of peak height absorbancies for various concentration of phosphate samples over the range 1–50 uM.

These effects can be seen clearly from the trace in FIG. 9, showing the absorbance monitored at 500 nm from the passage of a sample of 5M NaOH through the flow cell—an extreme example. In this case both the trough and the peak give rise to transmission changes of the order of 0.04 AU. In many cases, particularly where reagents are not so concentrated, reaction product absorbances may be much larger than the disturbances which arise from these sources. In such cases the monitored peak height is found to vary linearly with sample concentration over a substantial range of sample sizes. However, at low sample concentration these effects do give rise to a deviation from linearity. FIG. 10 shows the variation of peak height (in AU) with sample concentration for a series of analyses performed on samples of phosphate, using the reagents and monitoring wavelength described above. Significant deviations from linearity are apparent below $7 \times 10^{-6}$M [$PO_4^{3-}$]. Fortunately, such deviations can be removed by subtracting the signal recorded from a blank, which is relatively simple to arrange in software.

Even without such corrections, the sensitivity of the technique is high, approaching or exceeding the sensitivities of conventional flow analysis instruments. It will be apparent that the high reliability and reproducibility of the apparatus described, and its ability to select from a range of reagents under software control, provide significant advantages for routine analysis.

Figure 12:
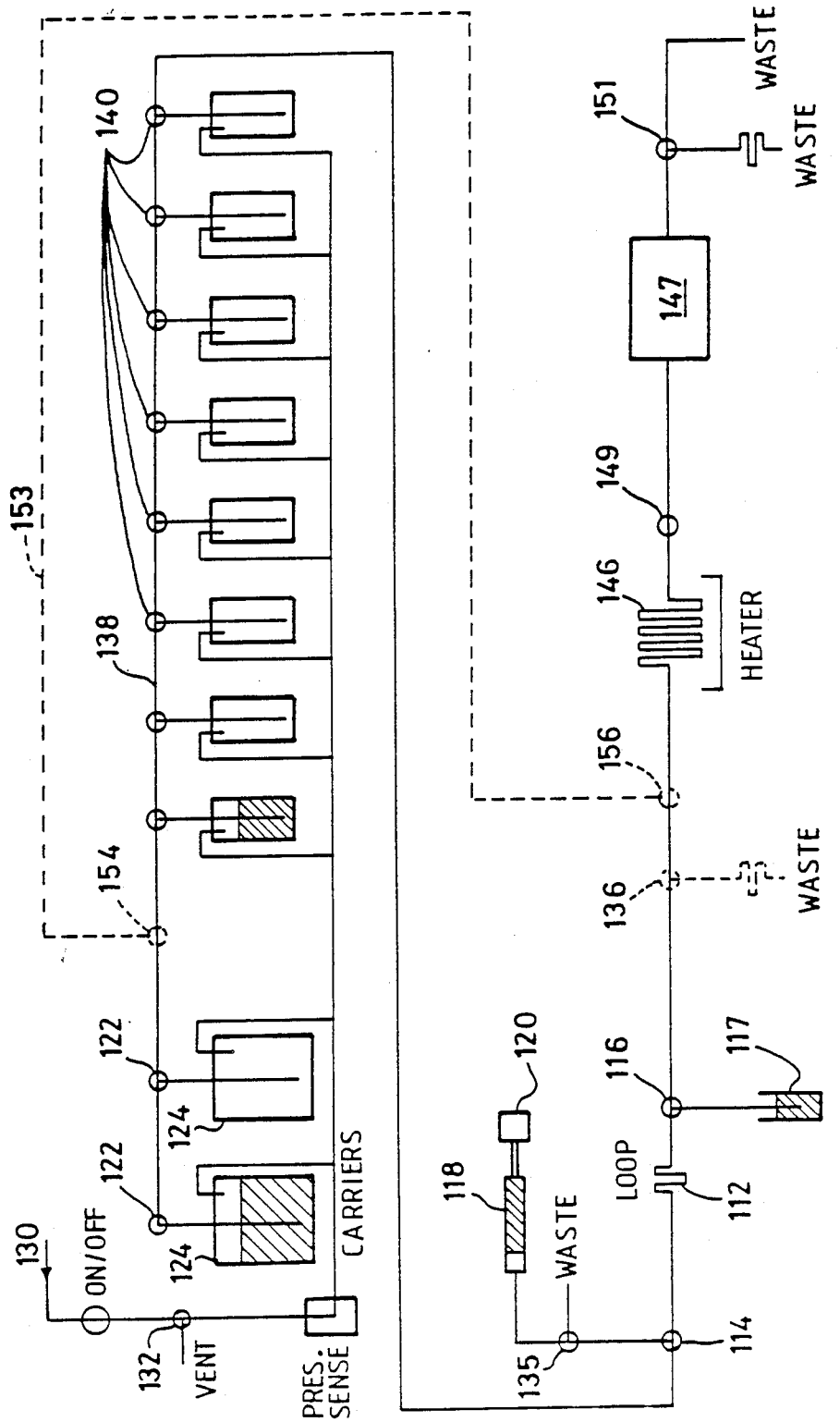
FIG. 12 shows a second embodiment of apparatus comparable with FIG. 1.

FIG. 12 shows a second embodiment of apparatus comparable with FIG. 1, and in which similar parts have been given the same references but increased by 100. At the outset is will be noted that the reagent manifold 138 is here positioned upstream of the sample duct 112. Carrier valves 122 allow a choice of principal carrier liquids, while valves 140 allow selected reagents, diluents or alternative carriers to enter the flow by replacing the principal carrier. By operating pairs of valves alternately at a frequency of 20 Hz it is possible to produce reagent mixtures in the manifold 138, and this technique is useful for reagent mixtures which would exhibit a short shelf life. The reagent or mixture selected for a particular determination is allowed to fill the manifold for a predetermined time period, referred to as the fill time, tf, controlled by the computer and defined by a software procedure written for the determination. At this point the sample duct or loop 112 which is bounded by valves 114 and 116, may be switched out of the manifold 138 and filled with a sample using the solenoid operated syringe pump 118. Excess liquid is expelled from the syringe pump 118 through valve 135 (similar to valve 34 of FIG. 1), so the pump 118 may be operated repeatedly to fill any desired loop volume. Once the sample loop is loaded the pathway between the reagent valve 140 on the right and the reaction tube 146 contains a sandwiched pattern of reagent-sample-reagent or reagent-carrier-sample which depends on the magnitude of tf and is of precisely reproducible volumes. The first pattern gives maximum sensitivity, while the second can be used for an automatic in-line dilution type of procedure in which only the highly dispersed portion of the sample zone mixes with reagent.

In the present system the loop volume was approximately 160 microliters (hereafter ul), and the system used up to about 400 ul of reagent mixture (when operating in maximum sensitivity mode) and a total of 400 ul of sample (including the volume in the sample delivery tube) for each analysis. It is likely that this latter volume could be made smaller, although it compares favourably with the actual sample usage in other automatic analysis systems. Closure of valves 114 and 116 causes this sample-containing sandwich to be passed through to the reaction tube 146 and ultimately to a detector 147. Once the reaction mixture is in the reaction tube, a valve 149 may be closed to stop the flow for a precisely controlled reaction time. As the reaction tube is maintained at a user-specified temperature, a wide variety of reaction times and temperatures may be used to accommodate a range of reaction chemistries. Certainly if the reaction is carried out at an elevated temperature, it is desirable that outlet valve 149 should be closed to avoid the formation of gas bubbles within the reaction tube 146. After a timed reaction period, valve 149 is opened and the reaction mixture passed through the detector system and to waste.

Beyond the detector flow cell is a valve 151, which permits a choice of two pathways to waste. In one pathway a relatively wide bore tube is used to carry the liquid flow, and under normal operating conditions (a gas pressure of approximately 15 psig or 1.05 kg/cm$^2$) the flow rate through this pathway is about 5 cm$^3$/min[1]. This fast flow rate is useful for initialising the instrument (which involves ensuring that the tubes between the reagent reservoirs and the manifold valves 140 contain fresh reagent) and for flushing the manifold 138 when changing chemistries or carriers. The second pathway is through a restricted coil of narrow bore tubing, and this provides a back pressure to the manifold and cuts the flow rate to approximately 2.5 cm$^3$/min. This flow rate is used for reagent mixing, reaction mixture propulsion and product measurement.

The important volumes, and hence the lengths of interconnecting tubing, are the sections between the valves 116 and valve 149 downstream of the reaction tubes 146 (the reaction tube volume), and that between valves 114 and 116 (the volume of the sample loop 112). In the present system these volumes are 160 and 500 ul respectively, obtained by using lengths of 50 and 120 cm of tubing. Other interconnecting tubes are maintained as short as is practical, allowing for considerable economy in the use of reagents.

In a modification of FIG. 12, an alternative by-pass path 153 (shown dotted) is provided from a three-way valve 154 downstream of carrier valve 122 and leading to a three-way valve 156 upstream of the reaction tube 146. This path enables carrier liquid to directly enter the reaction tube, and allows the reagent preparation to occur and the sample to be loaded while the previous reaction mixture is sitting in the reaction tube. The additional carrier pathway may then be used to initiate the passage of the reaction mixture to the detector 147. Valve 136 to waste would be required to allow the reagent manifold 138 to be filled while the previous reaction mixture was stationary in the reaction rube 146. This approach can reduce analysis times by up to 30 s per sample for reactions with at least a 30 s reaction time.

In a further modification of FIG. 12 (not shown) a second reaction tube is fitted in parallel with the main reaction tube 146, so that one reaction can be taking place while a second mixture is being passed on to the detector (and a third sample is being loaded). In this case all parts of the system are being used all the time, preparing reagents, loading sample, allowing reaction to occur and monitoring the product. This offers advantages because it is easier to mix hot and cold (or two different temperature) reactions within a multianalyte procedure.

We claim:

1. Apparatus for flow injection analysis, comprising:
   a sample duct of predetermined volume;
   a reaction tube;
   a carrier line connecting the sample duct and the reagent tube, whereby a sample to be analysed can be conveyed by pressurized carrier fluid with added reagent from the sample duct to the reagent tube;
   isolating valves upstream and downstream of the sample duct operable to stop the flow of carrier fluid and to isolate the sample duct from the carrier line;
   sample loading means comprising a solenoid operable syringe connected to the upstream isolating valve to suck a sample into the sample duct via the downstream isolating valve; and
   a waste valve positioned between the sample duct and the upstream valve, said waste valve enabling sample surplus to the said predetermined volume to be passed to waste.

2. Apparatus according to claim 1 in which said isolating valves comprise three-way valves, one being located on the upstream and one on the downstream side of the sample duct.

3. Apparatus according to claim 1 further including at least one valve on the upstream side of the upstream isolating valve to provide for the carrier line to be connected to any one of a plurality of carrier and/or flushing fluids.

4. Apparatus according to claim 1 including a three-way valve on the downstream side of the downstream isolating valve, said three-way valve used for priming, allowing for intake of a small amount of sample and its ejection to waste before loading the sample duct with a predetermined volume to be analysed.

5. Apparatus according to claim 1 and further including a reagent manifold having a series of three-way valves, each including means for connection with an individual reagent reservoir to enable reagent to be added to the sample.

6. Apparatus according to claim 1 further including a by-pass line connected between the carrier line and the reaction tube, to enable a reaction mixture to be passed on to a detector while sample loading takes place.

7. Apparatus according to claim 1 in which said reaction tube includes a thermostatic control means.

8. Apparatus according to claim 7 in which said reaction tube includes at its downstream end a three-way valve which is connected to waste and to an outlet leading to a detector.

9. Apparatus according to claim 1 including means for driving the carrier fluid and the reagent by positive pressure displacement.

10. Apparatus according to claim 9 in which said means for driving comprises a common gas inlet and an overpressure vent.

* * * * *